United States Patent
Nagy et al.

(10) Patent No.: US 9,617,233 B2
(45) Date of Patent: Apr. 11, 2017

(54) EPOXIDATION CATALYSTS BASED ON METAL ALKOXIDE PRETREATED SUPPORTS

(71) Applicant: Lyondell Chemical Technology, L.P., Houston, TX (US)

(72) Inventors: Sandor Nagy, Webster, TX (US); Vu A. Dang, Humble, TX (US); Roger A. Grey, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/044,210

(22) Filed: Feb. 16, 2016

(65) Prior Publication Data

US 2016/0237051 A1    Aug. 18, 2016

Related U.S. Application Data

(60) Provisional application No. 62/117,150, filed on Feb. 17, 2015.

(51) Int. Cl.

| | | |
|---|---|---|
| *C07D 301/19* | (2006.01) |
| *B01J 21/00* | (2006.01) |
| *B01J 23/00* | (2006.01) |
| *B01J 31/02* | (2006.01) |
| *B01J 31/38* | (2006.01) |
| *B01J 37/02* | (2006.01) |
| *B01J 35/02* | (2006.01) |
| *B01J 35/10* | (2006.01) |
| *B01J 21/06* | (2006.01) |
| *B01J 21/08* | (2006.01) |
| *B01J 29/03* | (2006.01) |
| *B01J 29/89* | (2006.01) |
| *B01J 37/00* | (2006.01) |

(52) U.S. Cl.
CPC .......... *C07D 301/19* (2013.01); *B01J 21/063* (2013.01); *B01J 21/08* (2013.01); *B01J 29/0308* (2013.01); *B01J 29/89* (2013.01); *B01J 31/0274* (2013.01); *B01J 31/38* (2013.01); *B01J 35/023* (2013.01); *B01J 35/1019* (2013.01); *B01J 35/1023* (2013.01); *B01J 35/1042* (2013.01); *B01J 35/1047* (2013.01); *B01J 37/0009* (2013.01); *B01J 37/0207* (2013.01); *B01J 37/0217* (2013.01); *B01J 2231/72* (2013.01)

(58) Field of Classification Search
CPC ..... C07D 301/06; C01B 37/005; C07C 29/03; B01J 37/0009; B01J 37/0207; B01J 37/0217; B01J 29/89; B01J 29/0308; B01J 21/08; B01J 31/0274; B01J 35/1042; B01J 35/1023; B01J 35/1019; B01J 35/023; B01J 2231/72
USPC ................................. 549/529; 502/232, 309
See application file for complete search history.

(56) References Cited

U.S. PATENT DOCUMENTS

| | | | |
|---|---|---|---|
| 6,114,552 A | 9/2000 | Han et al. | |
| 8,664,412 B2 | 3/2014 | Buijink | |
| 2009/0234143 A1 | 9/2009 | Yamamoto | |
| 2013/0116454 A1* | 5/2013 | Buijink | B01J 21/06 549/529 |

FOREIGN PATENT DOCUMENTS

| | | | |
|---|---|---|---|
| WO | WO9850374 | * | 11/1998 |
| WO | WO-2012010491 A1 | | 1/2012 |

OTHER PUBLICATIONS

The International Search Report and Written Opinion for PCT/US2016/018048 mailed May 4, 2016.

* cited by examiner

*Primary Examiner* — T. Victor Oh

(57) ABSTRACT

The present disclosure generally relates to a silica-titanium catalyst prepared by first reacting a solid support with a metal alkoxide and then depositing titanium onto the solid support for the epoxidation of alkenes and aralkenes and a method of preparing the catalyst thereof. In some embodiments, the present disclosure relates to methods of using the catalyst described herein for the production of epoxides.

17 Claims, No Drawings

EPOXIDATION CATALYSTS BASED ON METAL ALKOXIDE PRETREATED SUPPORTS

CROSS-REFERENCE TO RELATED APPLICATIONS

This application claims the benefit of priority to U.S. Provisional Application No. 62/117,150, filed on Feb. 17, 2015, which is incorporated herein by reference in its entirety.

BACKGROUND OF THE INVENTION

I. Technical Field

In some aspects, the present disclosure relates to epoxidation chemistry and catalysts thereof. The present disclosure relates to new titanium silica catalysts for use in the epoxidation of an alkene or aralkene and methods of preparing the catalysts.

II. Description of Related Art

Titanium silica catalysts represent one of the most commonly used catalysts for the production of epoxidation products from alkenes. In the presence of a peroxide, the catalyst assists in converting a carbon-carbon double bond into an epoxide. In general, there are three primary types of reactions which will lead to the generation of an appropriate titanium silica catalyst. The first reaction involves grafting the titanium species directly onto an oxide surface. Such a mechanism works by directly treating the solid support with a titanium complex such as titanium tetrachloride. Next, an appropriate catalyst can be produced by the hydrothermal synthesis of Ti-silicates, such as the commercially available TS-1 and Ti-MWW. Finally, the titanium silicates can also be formed through the use of non-hydrolytic sol-gel routes such as those based upon alkyl halide elimination.

These methods produce catalysts which exhibit moderate activity due to metal leaching, the presence of other metals in the reagents and final products, or other factors. As such, the further development of epoxidation catalysts and methods of preparation are commercially useful.

SUMMARY OF THE INVENTION

The present disclosure provides a catalyst and methods of preparing the same. In some embodiments, the catalysts are titanium silver catalysts and methods of preparing these catalysts are disclosed. Additionally, in another aspect, the present disclosure provides methods of using the titanium/silica catalyst to generate an epoxide.

In some aspects, the present disclosure provides a method of preparing a transition metal epoxidation catalyst, the method comprising:

a) obtaining a solid silica support;
b) reacting the solid silica support with a silicon alkoxide of the formula:

$$SiX_Y$$

wherein each X is independently halide, alkoxylate$_{(C \leq 12)}$, alkenyloxylate$_{(C \leq 12)}$, alkynyloxylate$_{(C \leq 12)}$, aryloxylate$_{(C \leq 12)}$, heteroaryloxylate$_{(C \leq 12)}$, aralkyloxylate$_{(C \leq 12)}$, aralkenyloxylate$_{(C \leq 12)}$, heterocycloalkyloxylate$_{(C \leq 12)}$, acyloxylate$_{(C \leq 12)}$, or a substituted version of any of these groups bearing a net negative charge; and Y is equal to the oxidation state of Si; and c) depositing titanium from a titanium source on the solid silica support thereby forming a catalyst.

In some embodiments, the solid silica support is a porous material. In some embodiments, the solid support has an average particle size from about 0.1 m to about 1.5 cm. In some embodiments, the solid support has an average particle size from about 0.7 mm to about 3.0 mm. In some embodiments, the solid silica support has a surface area between about 20 m$^2$/g and about 1500 m$^2$/g. In some embodiments, the solid silica support has a surface area between about 300 m$^2$/g and about 1100 m$^2$/g. In some embodiments, the solid silica support has a pore volume between about 0.1 mL/g and about 4.5 mL/g. In some embodiments, the solid silica support has a pore volume between about 0.5 mL/g and about 3.0 mL/g. In some embodiments, the solid silica support is an amorphous material. In some embodiments, the solid silica support is a zeolite. In some embodiments, the oxidation state of the silicon is a positive oxidation state.

In some embodiments, the silicon support contains a component having the formula:

$$SiX_4$$

wherein: each X is independently halide, alkoxylate$_{(C \leq 12)}$, aralkoxylate$_{(C \leq 12)}$, aryloxylate$_{(C \leq 12)}$, or a substituted version of any of these groups. In some embodiments, X is alkoxylate$_{(C \leq 12)}$. In some embodiments, X is methoxylate, ethyoxylate, isopropoxylate, or tert-butoxylate. In some embodiments, X is isopropoxylate. In some embodiments, the titanium source is a liquid or a gas. In some embodiments, the titanium source is titanium trihalide, titanium tetrahalide, or titanium tetraalkoxylate.

In some embodiments, the titanium source is titanium tetrachloride. In some embodiments, titanium deposited from the titanium source comprises between about 0.1 weight % and about 10 weight % of the catalyst. In some embodiments, the titanium deposited from the titanium source comprises between about 0.5 weight % and about 8 weight % of the catalyst. In some embodiments, the titanium deposited from the titanium source comprises between about 1 weight % and about 6 weight % of the catalyst. In some embodiments, the titanium deposited from the titanium source comprises about 5 weight % of the catalyst. In some embodiments, the method further comprises heating the catalyst to a temperature between about 250° C. and about 1000° C. In some embodiments, the temperature is between about 600° C. and about 900° C. In some embodiments, the temperature is about 700° C. In some embodiments, the catalyst is heated for a time period between about 0.5 and about 12 hours. In some embodiments, step c) is performed in an environment comprising oxygen. In some embodiments, the oxygen is from an ambient atmosphere. In other embodiments, step c) is performed in an environment comprising an inert gas. In some embodiments, the inert gas is nitrogen. In some embodiments, the method further comprises performing step c) in an environment comprising an inert gas and then again performing step c) in an environment comprising oxygen.

In another embodiment, the present disclosure provides a method of epoxidizing an olefin to produce an epoxide comprising:

a) obtaining a transition metal epoxidation catalyst; and
b) contacting the transition metal epoxidation catalyst with an alkene$_{(C \leq 20)}$ or aralkene$_{(C \leq 20)}$ and a peroxide in a reaction mixture under conditions sufficient to produce an epoxide.

In some embodiments, the alkene$_{(C \leq 20)}$ is an alkene$_{(C \leq 12)}$. In some embodiments, the alkene$_{(C \leq 12)}$ is ethylene, propylene, butylene, pentene, hexene, heptene, octene, nonene, or decene. In some embodiments, the alkene$_{(C \leq 12)}$ is propylene or octene. In some embodiments, the alkene$_{(C≤12)}$ is propylene. In some embodiments, the method further comprises heating the reaction mixture to a temperature between about 50° C. and about 250° C. In some embodiments, the reaction is heated to a temperature between about 50° C. and about 100° C. In some embodiments, the reaction is heated to about 70° C. In some embodiments, the reaction is heated to about 80° C. In some embodiments, the peroxide is tert-butyl hydroperoxide, ethylbenzyl hydroperoxide, or cumyl hydroperoxide. In some embodiments, the peroxide is tert-butyl hydroperoxide. In some embodiments, the epoxidation comprises a molar ratio of peroxide to alkene$_{(C≤20)}$ from about 1:2 to about 1:15. In some embodiments, the method further comprises adding a solvent to the reaction mixture. In some embodiments, the solvent is an organic solvent. In some embodiments, the solvent is an alcohol$_{(C≤12)}$. In some embodiments, the solvent is methanol, ethanol, isopropanol, and tert-butanol. In some embodiments, the method has a peroxide conversion of greater than 30%. In some embodiments, the peroxide conversion is greater than 50%. In some embodiments, the method has a peroxide selectivity of greater than 50%. In some embodiments, the peroxide selectivity is greater than 75%. In some embodiments, the peroxide selectivity is greater than 90%. In some embodiments, the peroxide selectivity is greater than 95%.

In another aspect, the present disclosure provides a transition metal epoxidation catalyst produced by a method comprising:

a) obtaining a solid support;

b) reacting the solid support with a silicon oxide of the formula:

SiX$_Y$ wherein: each X is independently halide, alkoxylate$_{(C≤12)}$, alkenyloxylate$_{(C≤12)}$, alkynyloxylate$_{(C≤12)}$, aryloxylate$_{(C≤12)}$, heteroaryloxylate$_{(C≤12)}$, aralkyloxylate$_{(C≤12)}$, aralkenyloxylate$_{(C≤12)}$, heterocycloalkyloxylate$_{(C≤12)}$, acyloxylate$_{(C≤12)}$, or a substituted version of any of these groups bearing a net negative charge; and Y is equal to the oxidation state of Si; and c) depositing titanium from a titanium source on the solid support.

In some embodiments, the solid support is a porous material. In some embodiments, the solid support comprises a solid silica support. In some embodiments, the solid support has an average particle size from about 0.1 m to about 1.5 cm. In some embodiments, the solid support has an average particle size from about 0.7 mm to about 3.0 mm. In some embodiments, the solid support has a surface area between about 20 m$^2$/g and about 1500 m$^2$/g. In some embodiments, the solid support has a surface area between about 300 m$^2$/g and about 1100 m$^2$/g. In some embodiments, the solid support has a pore volume between about 0.1 mL/g and about 4.5 mL/g. In some embodiments, the solid support has a pore volume between about 0.5 mL/g and about 3.0 mL/g. In some embodiments, the solid support is a zeolite. In some embodiments, the solid support is an amorphous material. In some embodiments, the oxidation state of the silicon is a positive oxidation state. In some embodiments, the silicon oxide has the formula:

SiX$_4$ wherein each X is independently halide, alkoxylate$_{(C≤12)}$, aralkoxylate$_{(C≤12)}$, aryloxylate$_{(C≤12)}$, or a substituted version of any of these groups. In some embodiments, X is alkoxylate$_{(C≤12)}$. In some embodiments, X is methoxylate, ethyoxylate, isopropoxylate, tert-butoxylate. In some embodiments, X is isopropoxylate. In some embodiments, the titanium source is a liquid or a gas. In some embodiments, the titanium source is titanium trihalide, titanium tetrahalide, or titanium alkoxylate. In some embodiments, the titanium source is titanium tetrachloride. In some embodiments, titanium deposited from the titanium source comprises between about 0.1 weight % and about 10 weight % of the catalyst. In some embodiments, titanium deposited from the titanium source comprises between about 0.5 weight % and about 8 weight % of the catalyst. In some embodiments, titanium deposited from the titanium source comprises between about 1 weight % and about 6 weight % of the catalyst. In some embodiments, titanium deposited from the titanium source comprises about 5 weight % of the catalyst. In some embodiments, the method further comprises heating the catalyst to a temperature between about 250° C. and about 1000° C. In some embodiments, the temperature is between about 600° C. and about 900° C. In some embodiments, the temperature is about 700° C. In some embodiments, the catalyst is heated for about 0.5 to about 12 hours. In some embodiments, step c) is performed in an environment comprising oxygen. In some embodiments, the oxygen is from the ambient atmosphere.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

DETAILED DESCRIPTION OF THE INVENTION

I. Alkene and Aralkene Epoxidation Reaction

While in no way limiting the scope of the present disclosure to any particular theory or theories, carbon-carbon double bonds generally react with hydrogen peroxide in the presence of a catalyst to form an epoxide. Such reactions can be used to generate an epoxide from a cis, trans or terminal double bond. In some embodiments, the present disclosure utilizes an alkene$_{(C2-60)}$ for epoxidation. In some embodiments, an alkene$_{(C2-20)}$ is utilized in the epoxidation reaction. In another embodiment, the alkene undergoing epoxidation is selected from propylene, butene, pentene, hexene, heptene, octene, nonene, decene, and their isomers. A broad number of conditions have been developed which can lead to an epoxide through the general reaction scheme shown below:

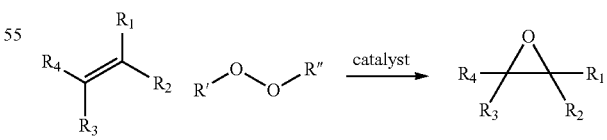

wherein R' and R" are each independently hydrogen, alkyl$_{(C≤50)}$, substituted alkyl$_{(C≤50)}$, aralkyl$_{(C≤50)}$, substituted aralkyl$_{(C≤50)}$, aryl$_{(C≤50)}$, or a substituted aryl$_{(C≤50)}$. In some embodiments, R' and R" are each independently hydrogen, aralkyl$_{(C≤24)}$, substituted aralkyl$_{(C≤24)}$, alkyl$_{(C≤24)}$, or substituted alkyl$_{(C≤24)}$. In some embodiments, R$_1$, R$_2$, R$_3$, and R$_4$ are hydrogen, substituted or unsubstituted alkyl$_{(C≤50)}$, or substituted or unsubstituted aryl$_{(C \leq 50)}$. In some embodiments, the alkyl group on $R_1$, $R_2$, $R_3$, or $R_4$ is a $C_2$-$C_{50}$ alkyl. In some embodiments, the alkyl group on $R_1$, $R_2$, $R_3$, or $R_4$ is $C_3$-$C_{20}$ alkyl. In other embodiments, the alkyl group on $R_1$, $R_2$, $R_3$, or $R_4$ is $C_3$-$C_{10}$ alkyl.

Furthermore, in some embodiments a peroxide is used for the epoxidation of the alkene. In some embodiments, the peroxide is an organic peroxide wherein R' and/or R" is an alkyl or aralkyl group. In some embodiments, the alkyl or aralkyl groups have 50 carbons. In some embodiments, the alkyl or aralkyl groups have between 3 and 20 carbons. In some embodiments, the organic peroxides that are used in the reaction of an alkene to form an epoxide include, but not limited to, for example, ethylbenzyl hydroperoxide, tert-butyl hydroperoxide, tert-amyl hydroperoxide, cyclohexyl hydroperoxide, and cumyl hydroperoxide. Additionally, in some embodiments, hydrogen peroxide (HOOH) can also be used in the epoxidation reactions presented herein. In some embodiments, the alkene to peroxide molar ratio can range from about 1:1 to about 20:1. In some embodiments, the range is from about 2:1 to about 15:1. In other embodiments, the peroxide is present in concentrations from about 1 to about 50% by weight of the epoxide reaction mixture including the olefin. In some embodiments, the ratio of olefin to peroxide can vary depending on other factors within the reaction mixture which might affect the stability of the peroxide. In some embodiments, the epoxidation reaction is carried out in the liquid phase with a heterogeneous titanium catalyst. In some embodiments, when an organic peroxide is used in the reaction, the reaction solvent comprises the organic byproduct of the synthesis or degradation of the peroxide. In a non-limiting example, if tert-butyl hydroperoxide is used, the solvent used in the reaction is tert-butanol, but the use of other solvents is possible.

In some embodiments, the catalyst contains a transition metal. The catalyst may be used to react with the carbon-carbon double bond to activate it towards attack with the peroxide or may be used to facilitate the breakdown of the peroxide into a more reactive intermediate. Furthermore, the catalyst may be used to increase the likelihood of the reaction of the formation of the desired epoxide product. In some embodiments, the catalyst used in the epoxidation reaction is a titanium catalyst. In some embodiments of the present disclosure, the titanium catalyst may contain other metals which further enhance the reactivity of the catalyst. In some embodiments, the olefin to epoxidation catalyst is used at the minimum concentration of the catalyst necessary to affect the desired transformation with an appropriate yield and selectivity. In some embodiments, titanium is present at a concentration of 0.1 wt % to 20 wt %. In some embodiments, the titanium is present at a concentration of 1 wt % to 10 wt %.

In some embodiments, epoxidation reactions may require moderate temperatures and pressures to proceed. In some embodiments, the reaction temperature is from about 0° C. to about 200° C. In some embodiments, the epoxidation reaction is carried out at an elevated temperature. The elevated temperature may be from about 25° C. to about 150° C. In some embodiments, the temperature of the epoxidation reaction is 70° C. In some embodiments of the present disclosure, the reaction is carried out at ambient pressure. In other embodiments, the epoxidation reaction is carried out at a pressure from 1 to 100 atmospheres.

In some embodiments, the reaction can be carried out in a liquid phase or a two phase (gas/liquid) system. Additionally, in some embodiments, the catalyst is a solid and represents a heterogeneous mixture with the alkene, the peroxide, the resultant epoxide and any solvents used to facilitate the reaction. As such, in some embodiments, the epoxidation reaction can be run on a commercial scale using a suitable reaction configuration including, but not limited to, continuous, batch or semi-continuous configurations. Conventional methods of product recovery including, but not limited to, fractional distillation, selective extraction, filtration or other methods may be used to obtain the desired product from the reaction mixture. In some embodiments, recovered materials such as catalyst, reactor solvent or unreacted olefin or peroxide can be recycled and reused. In some embodiments, the catalyst is used as a fixed bed in a flow-through reactor configuration.

The reaction can be evaluated based upon the rate of peroxide conversion and the extent of peroxide selectivity exhibited. In some embodiments, the peroxide conversion of the method of the present disclosure is greater than 10%. In some embodiments, the peroxide conversion of the method of the present disclosure is from about 10% to about 99.5%. In some embodiments, the peroxide conversion is from about 80% to about 99.5%. In some embodiments, the peroxide conversion is about 99%. In some embodiments, the peroxide selectivity of the method of the present disclosure is from about 90% to about 99.5%. In some embodiments, the peroxide selectivity is from about 95% to about 99.5%. In some embodiments, the peroxide selectivity is greater than 98%. In some embodiments, the peroxide conversion is greater than 50% and the peroxide selectivity is greater than 90%.

Atoms making up the catalysts of the present disclosure are intended to include all isotopic forms of such atoms. Catalysts of the present disclosure include those with one or more atoms that have been isotopically modified or enriched. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a catalyst of the present disclosure may be replaced by a silicon atom(s). Furthermore, it is contemplated that one or more oxygen atom(s) of a catalyst of the present disclosure can be replaced by sulfur or selenium atom(s).

II. Transition Metal Epoxidation Catalysts

The epoxidation reaction may further comprise using a transition metal catalyst which helps to facilitate the reaction and increase the yield of the desired products. In some embodiments, such transition metal catalysts contain a titanium atom which forms the reactive species with the alkene or aralkene. A catalyst may contain between 0.01% and 20% by weight of titanium relative to the total weight of the catalyst. In some embodiments, the catalyst may contain between 0.1% and 10% by weight of titanium relative to the total weight of the catalyst. In some embodiments, the catalyst contains between 1% and 7% by weight of titanium relative to the total weight of the catalyst. In some embodiments, the catalyst contains between 3% and 7% by weight of titanium relative to the total weight of the catalyst. In some embodiments, the inert solid support is an amorphous silica. In other embodiments, the solid support is a mesoporous silica such as, but not limited to, MCM-41. In some embodiments, the solid support is a molecular sieve such as a silicalites. Titanium doped silica supports or zeolites of the MWW family and their synthesis are known in the prior art, e.g. U.S. Pat. Nos. 6,759,540 and 8,124,555, which are incorporated herein by reference. In some embodiments, the solid support comprises approximately 80 to 99.99% by weight of the catalyst as a percentage of the total weight of the catalyst. In some embodiments, the solid support comprises 90% to 99.9% by weight of the catalyst as a percentage of the total weight of the catalyst. In some embodiments, the solid support comprises 90% to 99% by weight of the catalyst as a percentage of the total weight of the catalyst. In some embodiments, the solid support comprises 93% to 97% by weight of the catalyst as a percentage of the total weight of the catalyst. In some embodiments, the solid support is dried at a temperature from about 50° C. to about 400° C. In some embodiments, the solid support is dried at a temperature from about 100° C. to about 250° C. In some embodiments, the solid support is dried for a time period from about 0.5 hours to about 8 hours. In some embodiments, the time period is about 1 hour to about 4 hours.

In some aspects of the present disclosure, the inert solid support is siliceous solid, alumina, inorganic oxides, carbon or organic polymers. In some embodiments, the solid support may be a siliceous solid including but not limited to synthetic porous silicas, silica powders, refractory oxides, mesoporous molecular sieves, essentially pure silica and other siliceous solids. In some embodiments, the inert solid support is comprised of silicon dioxide ($SiO_2$). In some embodiments, the inert solid support is comprised of amorphous silicon dioxide ($SiO_2$).

In some embodiments, the solid support is a synthetic porous silica such as silica gel or precipitated silica. In some embodiments, the synthetic porous silicas comprise particles of amorphous silica that are flocculated or linked together such that the particles form a relatively dense and close packed core which have numerous pores, voids, or interstices that run throughout the structure. In other embodiments, the solid support is a synthetic silica powder. In some embodiments, the synthetic silica powder includes but is not limited to fumed, pyrogenic silicas from the reaction of a silicon halide with hydrogen and oxygen. In some embodiments, the synthetic silica powders comprise particles of amorphous silica in loose, open packed aggregates which are readily disintegrated. In another embodiment, the solid support is a refractory oxide including but not limited to silica-aluminas, silica-magnesias, silica-zirconias, silica-alumina-borias, silica-alumina-magnesias and similar compounds. In some embodiments, these oxide compounds contain a significant weight percentage of silica. In other embodiments, the solid support is a molecular sieve including but not limited to MCM-41, MCM-48, M41S, ZSM-5, XSM-11 and the MWW class of molecular sieves. In other embodiments, the solid support is pure silica, wherein pure silica is defined as being at least 95% silica by weight. In some embodiments, the amount of pure silica is greater than 97% silica. In some embodiments, the amount of pure silica is greater than 99% silica. Essentially pure silica can be obtained commercially. In some embodiments, suitable pure silica include but are not limited to suitable silicas sold by Davisil® such as Davisil® 643 and microspherical silica gels sold by PQ Corporation including MS-3050 silica. In other embodiments, the solid support comprises naturally occurring mineral silica including but not limited to hydrotalcites, hydrous magnesium silicates and clay minerals such as hectorites, kaolins and bentonites.

In some embodiments, the inert solid has a surface area from about 10 to about 1500 $m^2/g$. In some embodiments, the inert solid has a surface area from about 200 $m^2/g$ to about 1100 $m^2/g$. In some embodiments, the inert solid has a surface area of at least 1000 $m^2/g$. In some embodiments, the inert solid has a pore volume in the range of 0.5 to 8.0 mL/g. In some embodiments, the pore volume is from about 1.0 mL/g to about 4.0 mL/g. In some embodiments, the pore volume is from 1.0 mL/g to about 3.0 mL/g. While the size of the inert solid particles can vary depending on other reaction condition, in some embodiments, the average particle size is from about 0.1 μm to about 1.5 cm. Additionally, in some embodiments, the pore diameter of the catalytic material can vary but the average pore size of the inert solid is from 1 to about 1000 Å. In some embodiments, the average pore size of the inert solid is from about 50 to 500 Å.

In some aspects of the present disclosure, the solid support is a variety of different physical forms including but not limited to powders, flakes, granules, spheres and pellets. In some embodiments, the solid support originates in one form and may be used in that form or the solid support is converted into a different form through techniques known to those of skill in the art. Such conventional techniques include but are not limited to extrusion, pelletization and grinding.

In some embodiments, the titanium source for the deposition of the catalytically active titanium atoms is a titanium halide, titanium alkoxide or mixtures thereof. In some embodiments, the titanium source is a titanium halide or titanium alkoxide in which the titanium metal is in the $4^+$ oxidation state. In some embodiments, the titanium source for incorporation into the inert solid is a titanium tetrahalide. In some embodiments, the titanium source is titanium tetrachloride. In some embodiments, the titanium tetrachloride is used as a gas or as a part of a solution with an appropriate solvent. Appropriate solvents include hydrocarbon or aromatic solvents. In additional embodiments, commercially available solutions of titanium tetrachloride can be used as a source of titanium.

In some aspects of the present disclosure, the inert solid is also reacted with a silicon compound of the formula $SiX_Y$ wherein: each X is independently halide, alkoxylate$_{(C \leq 12)}$, alkenyloxylate$_{(C \leq 12)}$, alkynyloxylate$_{(C \leq 12)}$, aryloxylate$_{(C \leq 12)}$, heteroaryloxylate$_{(C \leq 12)}$, aralkyloxylate$_{(C \leq 12)}$, aralkenyloxylate$_{(C \leq 12)}$, heterocycloalkyloxylate$_{(C \leq 12)}$, acyloxylate$_{(C \leq 12)}$ or a substituted version of any of these groups bearing a net negative charge; and Y is equal to the oxidation state of Si. In some embodiments, the silicon compound has a formula $SiX_4$ wherein: each X is independently halide, alkoxylate$_{(C \leq 12)}$, aralkoxylate$_{(C \leq 12)}$, aryloxylate$_{(C \leq 12)}$ or a substituted version of any of these groups. In some embodiments, the inert solid is treated with the silicon compound before titanation. In some embodiments, the inert solid is treated with the silicon compound at the same time as titanation. In some embodiments, the inert solid is treated with the silicon compound after titanation. In some embodiments, the inert solid is reacted with the silicon compound in the presence of a solvent. In some embodiments, the solvent is a hydrocarbon$_{(C \leq 12)}$. In some embodiments, the solvent is hexanes. In some embodiments, the reaction with the silicon compound is under an inert atmosphere. In some embodiments, the inert atmosphere is a noble gas, nitrogen, carbon dioxide or a $C_1$-$C_8$ hydrocarbon. In some embodiments, the inert atmosphere is nitrogen.

In some aspects of the present disclosure, the inert solid is calcined before, after or during the incorporation of the titanium. In some embodiments, the inert solid is calcined at a temperature from about 500° C. to about 1000° C. In some embodiments, the calcination is carried out at a temperature from about 600° C. to about 800° C. Additionally, in some embodiments, the calcination may take place under an inert atmosphere. In some embodiments, the inert atmosphere is under helium, argon, neon or nitrogen. In some embodiments, the inert atmosphere is nitrogen. In some embodiments, calcination in an inert atmosphere is followed by calcination in air. In some embodiments, the calcination is performed for about 0.1 to about 24 hours. In some embodiments, the calcination is performed for about 1 to 18 hours. In some embodiments, the calcination is for about 1 to 4 hours. In some embodiments, the calcination changes the peroxide conversion percentage or the peroxide selectivity of a given catalyst and in a given catalytic system. In some embodiments, the calcination increases the peroxide conversion and the peroxide selectivity of a given reaction.

In some embodiments, the transition metal catalyst comprises an additional metal or metalloid in addition to the titanium. The metals that may be used are germanium, gallium, silicon and similar transition metals and metalloids.

III. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

IV. Definitions

When used in the context of a chemical group: "hydrogen" means —H; "hydroxy" means —OH; "oxo" means =O; "carbonyl" means —C(=O); "carboxy" means —C(=O)OH (also written as —COOH or —CO$_2$H); "halo" means independently —F, —Cl, —Br or —I; and "amino" means —NH$_2$. When used in the context of a chemical group: "carboxylate" means a molecule which contains the group, —C(=O)O$^-$ (also written as C(O)O$^-$ or —CO$_2^-$) and the overall charge of the molecule is negative, or "halide" means a halogen atom formulated as an anion bearing a single negative charge. Any undefined valency on an atom of a structure shown in this application implicitly represents a hydrogen atom bonded to that atom.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula

includes

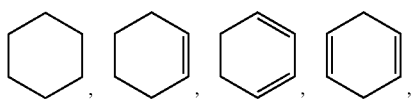

and

It is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " $\sim\sim$ ", when drawn perpendicularly across a bond

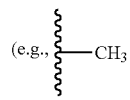

for methyl), indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol " ⦀ " means a single bond where the group attached to the thick end of the wedge is "into the page". The symbol " $\sim\sim$ " means a single bond where the geometry around a double bond (e.g., either E or Z) is undefined. Both options, as well as combinations thereof, are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M====C, each refers to a bond of any type and order between a metal atom and a carbon atom.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon-oxygen double bonds or a carbon-nitrogen double bond may be present. When such a bond is present, carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo-, cyclic or acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, —CH$_2$CH$_2$CH$_2$—, and

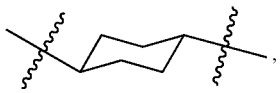 [SMILES: *C1CCC(*)CC1]

are non-limiting examples of alkanediyl groups. It is noted that while the alkenediyl group is aliphatic, once connected at both ends, this group is not precluded from forming an aromatic structure. The term "alkylidene" when used without the "substituted" modifier refers to the divalent group =CRR', in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as defined above. When any of these terms is used with the "substituted" modifier, one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$ or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group —CH$_2$Cl is a non-limiting example of a haloalkyl. The term "fluoroalkyl" is a subset of substituted alkyl, in which one or more hydrogen has been substituted with a fluoro-group, and no other atoms aside from carbon, hydrogen and fluorine are present. The groups —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo-, cyclic or acyclic structure, at least one nonaromatic carbon-carbon double bond, no carbon-carbon triple bonds and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo-, cyclic or acyclic structure, at least one nonaromatic carbon-carbon double bond, no carbon-carbon triple bonds and no atoms other than carbon and hydrogen. The groups —CH=CH—, —CH=C(CH$_3$)CH$_2$—, —CH=CHCH$_2$—, and

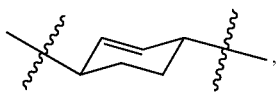 [SMILES: *C1C=CC(*)CC1]

are non-limiting examples of alkenediyl groups. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$ or —S(O)$_2$NH$_2$. The groups —CH=CHF, —CH=CHCl and —CH=CHBr, are non-limiting examples of substituted alkenyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s), wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl or alkenediyl groups (carbon number limitation permitting). Non-limiting examples of arenediyl groups include:

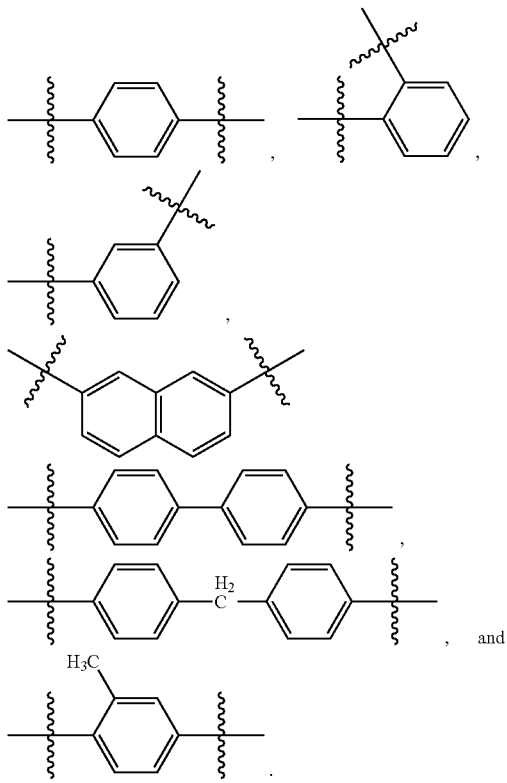

An "arene" refers to the compound H—R, wherein R is aryl as that term is defined above. Benzene and toluene are non-limiting examples of arenes. When any of these terms are used with the "substituted" modifier one or more hydrogen atoms has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃ or —S(O)₂NH₂.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl and triazolyl.

The term "N-heteroaryl" refers to a heteroaryl group with a nitrogen atom as the point of attachment. The term "heteroarenediyl" when used without the "substituted" modifier refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl or alkenediyl groups (carbon number limitation permitting). As used herein, the term does not preclude the presence of one or more alkyl, aryl and/or aralkyl groups (carbon number limitation permitting) attached to the aromatic ring or aromatic ring system. Non-limiting examples of heteroarenediyl groups include:

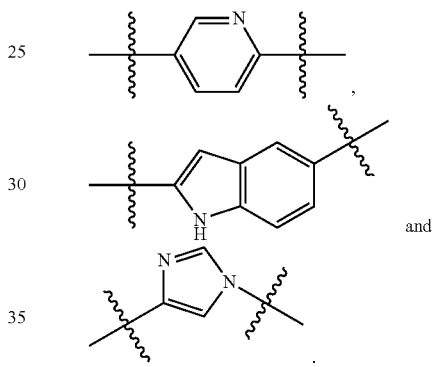

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃ or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl.

The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

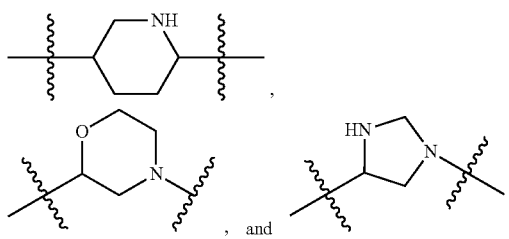

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atoms from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl and 2-chloro-2-phenyl-eth-1-yl.

The term "aralkenyl" when used without the "substituted" modifier refers to the monovalent group -alkenediyl-aryl, in which the terms alkenediyl and aryl are each used in a manner consistent with the definitions provided above. Non-limiting examples of aralkenyls are: 2-phenylethenyl and 3,3-diphenyl-prop-2-enyl. The term "aralkene" refer to a compound having the formula H—R, wherein R is aralkenyl as this term is defined above. A "terminal aralkene" refers to an aralkene having just one non-aromatic carbon-carbon double bond, wherein that bond forms a vinyl group at one end of the molecule. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$ or —S(O)$_2$NH$_2$. Non-limiting examples of substituted aralkenyls are: (3-nitrophenyl)-ethenyl and 4-cyano-4-phenyl-but-1-enyl.

The term "acyl" when used without the "substituted" modifier refers to the group —C(O)R, in which R is a hydrogen, alkyl, aryl, aralkyl or heteroaryl, as those terms are defined above. The groups —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$ and —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atoms (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$ or —S(O)$_2$NH$_2$. The groups —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl and —O-cyclohexyl. The terms "alkenyloxy", "alkynyloxy", "aryloxy", "aralkoxy", "heteroaryloxy", "heterocycloalkoxy" and "acyloxy", when used without the "substituted" modifier, refers to groups defined as —OR, in which R is alkenyl, alkynyl, aryl, aralkyl, heteroaryl, heterocycloalkyl, and acyl, respectively. The term "alkoxylate" when used in the context of this application, refers to the negatively charged group OR, in which R is an alkyl group as defined above. The terms "alkenyloxylate", "alkynyloxylate", "aryloxylate", "aralkoxylate", "aralkenyloxylate", "heteroaryloxylate", "heterocycloalkyloxylate" and "acyloxylate" refers to the groups, defined as OR, in which R is defined as an alkenyl, alkynyl, aryl, aralkyl, aralkenyl, heteroaryl, heterocycloalkyl, and acyl, respectively. Unless otherwise indicated, these "oxylate" terms include both substituted and unsubstituted groups. The term "alkoxydiyl" refers to the divalent group —O-alkanediyl-, —O-alkanediyl-O— or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$ or —S(O)$_2$NH$_2$.

The use of the word "a" or "an," when used in conjunction with the term "comprising" in the claims and/or the specification, may mean "one," but it is also consistent with the meaning of "one or more," "at least one" and "one or more than one."

Throughout this application, the term "about" is used to indicate that a value includes the inherent variation of error for the device, the method being employed to determine the value or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "epoxide" references to a three-membered ring containing at one oxygen atom and two carbon atoms joined by single bonds. An "epoxidation reaction" is a reaction which leads to the generation of an epoxide on the molecule. The most common epoxidation reaction results from converting an alkene or aralkene functional group within a molecule into an epoxide group.

An "isomer" of a first compound is a separate compound in which each molecule contains the same constituent atoms as the first compound, but where the configuration of those atoms in three dimensions differs.

A "method" is series of one or more steps that lead to a final product, result or outcome. As used herein, the word "method" is used interchangeably with the word "process".

A "peroxide" is a molecule containing a single covalent bond between two oxygen atoms and each oxygen is also bound to a hydrogen, alkyl, alkenyl, alkynyl, aryl, aralkyl, heteroaryl or heterocycloalkyl group as those groups are defined above and contains between 1 and 30 carbon atoms. In some embodiments, a hydroperoxide is a compound containing a single covalent bond between two oxygen atoms, and one of the oxygen atoms is bound to a hydrogen atom and the other oxygen is bound to an alkyl, alkenyl, alkynyl, aryl, aralkyl, heteroaryl or heterocycloalkyl group as those groups are defined above and contains between 1 and 20 carbon atoms. Some non-limiting examples of hydroperoxides include ethylbenzene hydroperoxide, tert-amylhydroperoxide, cyclohexyl hydroperoxide, and cumeme hydroperoxide. In general, the peroxide bond between the two oxygen atoms is generally labile and readily decomposes or reacts with other molecules. Some non-limiting examples of peroxides include HO—OH (hydrogen peroxide) and $(CH_3)_3CO$—OH (tert-butyl hydroperoxide).

The "peroxide conversion percentage" is a measurement of the amount of peroxide consumed in the reaction. This measurement can be used to compare the efficacy of a given reaction and as a measure of the amount of reagent consumed in the production of the desired product.

A "solid support" or "carrier" relate to an inert material on which the metal catalyst or other reagents can be deposited but does not degrade or consume the reagents or metal catalyst. In some instances, the solid support or carrier can be silica, alumina, organic polymers, or other non-reactive materials with a high surface area and are generally have a high porosity. Additionally, in some embodiments, the solid support or carrier contains numerous pores, voids or other interstices throughout its structure. In some embodiments, the silica particles may contain particles which are flocculated or linked together into a dense, close-packed mass or are contain an loosely-knit and readily disintegrated into open-packed aggregates. The support or carrier can be used to bind the catalytically active atoms or complexes. In some embodiments, the major portion of the solid support is silicon dioxide ($SiO_2$) and amorphous forms of $SiO_2$. In some non-limiting examples, the solid support is a silica compound that is commercially available for various purposes including, but not limited to, thin layer chromatography, column chromatography, catalyst support or another commercial use. In some instances, the solid support is a silica gel such as the Davisil® 643 porous material or similar commercially available materials. In some embodiments, the solid support is a mesoporous silica such as MCM-41 or SBA-15.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

V. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Catalyst Testing Procedure

A 14 mL aliquot of a reaction mixture prepared by combining 88.03 g of 1-octene, 10.49 g TBHP oxidate (41% TBHP in isopropyl alcohol) and 3.24 g of nonane (internal standard) was placed in a three-neck flask equipped with a condenser and a magnetic stirrer and heated to 80° C. under $N_2$ atmosphere. The reaction started by adding 50 mg of dry catalyst to the reaction mixture. A sample was collected by a needle/syringe via a septum after 60 minutes. As a measure of the efficacy of the catalyst, the conversion of peroxide for each catalyst is measured. The peroxide content was measured using iodometric titration and the composition was determined using GC chromatography.

Example 2: Preparation and Comparison of Different Titanium Silica Catalysts in a TBHP Epoxidation Reaction Example A Epoxidation Testing of Ti-MWW Titanosilicate: the Ti-MWW Catalyst prepared according to U.S. Pat. No. 8,124,555 was tested according to the standard testing procedure resulted in a 37% conversion of TBHP to 1,2-epoxyoctene with >98% selectivity.

Example B

Preparation of Silica D643 Titanated by $TiCl_4$ and Epoxidation Testing: 0.5 g of Davisil® 643 silica (Sigma Aldrich, 200-425 mesh, pore size 150 Å, surface area 300 m²/g) was placed in a quartz calcination tube under a N₂ flow of 100 mL/min and dried for 2 hours at 200° C. After cooling to ambient temperature, 1.5 mL of 1 M TiCl₄ solution in toluene was added slowly to the top of the silica bed, followed by 3 mL of dry toluene. The tube was gradually heated to 800° C. under a flow of 100 mL/min of N₂ using the following program: 10 min at 60° C.→15 min at 200° C.→60 min at 600° C.→30 min at 700° C.→30 min at 800° C. The catalyst tested according to the standard testing procedure resulted in a 40% conversion of TBHP to 1,2-epoxyoctene.

Example C

Preparation of Mesoporous Silica MCM-41 Titanated by TiCl₄ and Epoxidation Testing: 0.5 g of MCM-41 mesoporous silica (Sigma Aldrich; 2.1-2.7 nm pore size; surface area ~1000 m²/g) was placed in a quartz calcination tube under N₂ flow of 100 mL/min and dried 2 hours at 200° C. After cooling to ambient temperature 1.0 mL of 1M TiCl₄ solution in hexane was added slowly to the top of the silica bed followed by 3 mL of dry toluene. The tube was gradually heated to 800° C. under a flow of 100 mL/min of N₂ using the following program: 30 min at 25° C.→15 min at 200° C.→60 min at 600° C.→30 min at 700° C.→30 min at 800° C. The catalyst tested according to the standard testing procedure resulted in a 52% conversion of TBHP to 1,2-epoxyoctene with >98% selectivity.

Example D

Preparation of Non-Hydrolytic Ti—SiO₂ Sol-Gel Supported on Silica D643 and Epoxidation Testing: A mixture of 0.55 mL of SiCl₄, 1.19 mL of Si(OiPr)₄ and 0.26 mL of Ti(OiPr)₄ (Similar method used by Lafond et al., which is incorporated herein by reference) was impregnated into a 3 g Davisil® 643 silica (Sigma Aldrich, 200-425 mesh, pore size 150 Å, surface area 300 m²/g) sample dried for 2 h at 200° C. The resulting slightly wet powder was placed into a 25 mL stainless steel Parr micro-reactor under N₂ atmosphere and heated to 110° C. internal temperature for 2 h 45 min (165 min). The reaction was continued the following day for 6 h 30 min (390 min) at an internal temperature of 150° C. The reactor was cooled to ambient temperature and degassed. 0.8 g of the resulting material was placed in a quartz calcination tube and gradually heated to 800° C. under a flow of 100 mL/min of N₂ using the following program: 10 min at 100° C.→15 min at 200° C.→60 min at 600° C.→30 min at 700° C.→30 min at 800° C. The catalyst tested according to the standard testing procedure resulted in a 8% conversion of TBHP to 1,2-epoxyoctene with >98% selectivity.

Example E

Preparation of Silica D643 Titanated with a Si(OiPr)₄—TiCl₄ Mixture and Epoxidation Testing: 0.5 g of Davisil® 643 silica (Sigma Aldrich, 200-425 mesh, pore size 150 Å, surface area 300 m²/g) was placed in a quartz calcination tube under N₂ flow of 100 mL/min and dried 2 hours at 200° C. After cooling to ambient temperature, a mixture of 0.3 mL (0.264 g; 0.001 mol) Si(OiPr)₄ and 0.5 ml of 1 M TiCl₄ solution in toluene was added slowly to the top of the silica bed. The tube was gradually heated to 800° C. under a flow of 100 ml/min of N₂ using the following program: 30 min at 50° C.→45 min at 80° C.→20 min at 100° C.→25 min at 200° C.→60 min at 600° C.→30 min at 700° C.→45 min at 800° C. The catalyst tested according to the standard testing procedure resulted in a 48% conversion of TBHP to 1,2-epoxyoctene with 57% selectivity.

Example F

Preparation of Silica D643 Pretreated with a Si(OiPr)₄ and Titanated by TiCl₄ and Epoxidation Testing: 0.5 g of Davisil® 643 silica (Sigma Aldrich, 200-425 mesh, pore size 150 Å, surface area 300 m²/g) was placed in a quartz calcination tube under N₂ flow of 100 mL/min and dried 2 hours at 200° C. After cooling to ambient temperature, 0.3 mL (0.264 g; 0.001 mol) of Si(OiPr)₄ was added slowly to the top of the silica bed followed by 1 mL of dry toluene. 1 mL of 1 M TiCl₄ solution was added to the top of the silica bed in two portions and the silica bed was washed with toluene. The tube was gradually heated to 800° C. under a flow of 100 mL/min of N₂ using the following program: 15 min at 50° C.→15 min at 100° C.→15 min at 200° C.→60 min at 600° C.→30 min at 700° C.→30 min at 800° C. The catalyst tested according to the standard testing procedure resulted in a 48% conversion of TBHP to 1,2-epoxyoctene with 96% selectivity.

Example G

Preparation of MCM-41 Mesoporous Silica Pretreated with a Si(OiPr)₄ and Titanated by TiCl₄ and Epoxidation Testing: 0.5 g of MCM-41 mesoporous silica (Sigma Aldrich; 2.1-2.7 nm pore size; surface area ~1000 m²/g) was placed in a quartz calcination tube under N₂ flow of 100 mL/min and dried for 2 hours at 200° C. After cooling to ambient temperature, 0.3 mL (0.264 g; 0.001 mol) of Si(OiPr)₄ was added slowly to the top of the silica bed followed by 2 mL of dry hexane. 0.3 mL of neat TiCl₄ was added to the top of the silica bed then washed with 3 mL of hexane. The tube was gradually heated to 800° C. under a flow of 100 mL/min of N₂ using the following program: 15 min at 50° C.→15 min at 100° C.→15 min at 200° C.→60 min at 600° C.→30 min at 700° C.→30 min at 800° C. The catalyst tested according to the standard testing procedure resulted in a 59% conversion of TBHP to 1,2-epoxyoctene with >98% selectivity.

TABLE 1

Summary of Epoxidation with Different Catalysts

| Example | Catalyst Type | TBHP Conversion, % | Selective to Epoxide, % |
|---|---|---|---|
| A | Ti-MWW - Hydrolytic Ti—SiO₂ | 37 | >98 |
| B | Ti-grafted on SiO₂ | 40 | |
| C | Ti-grafted on mesoporous SiO₂ | 52 | >98 |
| D | Non-hydrolytic Ti—SiO₂ supported on SiO₂ | 8 | >98 |
| E | SiO₂ titanated by Si(OiPr)₄—TiCl₄ mix. | 48 | 57 |
| F | SiO₂ pretreated with Si(OiPr)₄ before titanated | 48 | 96 |
| G | Mesoporous SiO₂ pretreated with Si(OiPr)₄ before titanated | 59 | >98 |

All of the compounds, complexes, and methods disclosed and claimed herein can be made and executed without undue experimentation in light of the present disclosure. While the compounds, complexes, and methods of this disclosure have been described in terms of preferred embodiments, it will be apparent to those of skill in the art that variations may be applied to the compounds, complexes, and methods, as well as in the steps or in the sequence of steps of the method described herein without departing from the concept, spirit, and scope of the disclosure. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

U.S. Pat. No. 6,759,540
U.S. Pat. No. 8,124,555
Anderson, N. G., *Practical Process Research & Development—A Guide For Organic Chemists*, 2nd ed., Academic Press, New York, 2012.
Lafond, et al., *J. of Molecular Catalyst*, 182-183:81-88, 2002.
*March's Advanced Organic Chemistry: Reactions, Mechanisms, and Structure*, 2007.

What is claimed is:

1. A method comprising:
   a) obtaining a solid silica support;
   b) reacting the solid silica support with a silicon alkoxide of the formula:

$SiX_Y$;

wherein:
      each X is independently halide, alkoxylate$_{(C\leq12)}$, alkenyloxylate$_{(C\leq12)}$, alkynyloxylate$_{(C\leq12)}$, aryloxylate$_{(C\leq12)}$, heteroaryloxylate$_{(C\leq12)}$, aralkyloxylate$_{(C\leq12)}$, aralkenyloxylate$_{(C\leq12)}$, heterocycloalkyloxylate$_{(C\leq12)}$, acyloxylate$_{(C\leq12)}$, or a version of any of these groups bearing a net negative charge; and
      Y is equal to the oxidation state of Si; and
   c) depositing titanium from a titanium source on the solid silica support reacted with a silicon alkoxide to form a catalyst in an initial environment comprising an inert gas and then an environment comprising oxygen.

2. The method of claim 1, wherein the solid silica support has an average particle size of 0.7 mm-3.0 mm.

3. The method of claim 1, wherein the solid silica support has a surface area of 300-1100 m$^2$/g.

4. The method of claim 1, wherein the solid silica support has a pore volume of 0.5-3.0 mL/g.

5. The method of claim 1, wherein the silicon alkoxide has the formula:

$SiX_4$;

wherein:
      each X is independently halide, alkoxylate$_{(C\leq12)}$, aralkoxylate$_{(C\leq12)}$, aryloxylate$_{(C\leq12)}$, or a version of any of these groups bearing a negative charge.

6. The method of claim 5, wherein X is selected from the group consisting of methoxylate, ethyoxylate, isopropoxylate and tert-butoxylate.

7. The method of claim 1, wherein the titanium source is selected from the group consisting of titanium trihalide, titanium tetrahalide and titanium tetraalkoxylate.

8. The method of claim 1, wherein titanium deposited from the titanium source comprises 0.1-10% by weight of the catalyst.

9. The method of claim 1, wherein the method further comprises heating the catalyst to a temperature of 250-1000° C.

10. The method of claim 9, wherein the catalyst is heated for a time period of 0.5-12 hours.

11. The method of claim 1, wherein the inert gas is nitrogen.

12. A method for producing an epoxide comprising:
   contacting the catalyst of claim 1 with an alkene$_{(C\leq20)}$ or aralkene$_{(C\leq20)}$ and a peroxide in a reaction mixture under conditions sufficient to cause olefin epoxidation to produce an epoxide.

13. The method of claim 12, wherein the alkene$_{(C\leq20)}$ is propylene.

14. The method of claim 12, further comprising heating the reaction mixture to a temperature from 50-250° C.

15. The method of claim 12, wherein the peroxide is selected from the group consisting of tert-butyl hydroperoxide, ethylbenzyl hydroperoxide and cumyl hydroperoxide.

16. The method of claim 12, wherein the epoxidation comprises a molar ratio of peroxide to alkene$_{(C\leq20)}$ from 1:2-1:15.

17. The method of claim 12, further comprising adding a solvent selected from the group consisting of methanol, ethanol, isopropanol and tert-butanol to the reaction mixture.

* * * * *

UNITED STATES PATENT AND TRADEMARK OFFICE
CERTIFICATE OF CORRECTION

PATENT NO. : 9,617,233 B2  
APPLICATION NO. : 15/044210  
DATED : April 11, 2017  
INVENTOR(S) : Sandor Nagy et al.

Page 1 of 1

It is certified that error appears in the above-identified patent and that said Letters Patent is hereby corrected as shown below:

In the Specification

| | | |
|---|---|---|
| Column 2 | Line 3 | Delete "m" and insert --µm-- |
| Column 18 | Line 58 | Delete "the" and insert --The-- |
| Column 18 | Line 59 | Delete "Catalyst" and insert --catalyst-- |

Signed and Sealed this  
Twenty-second Day of October, 2019

Andrei Iancu  
*Director of the United States Patent and Trademark Office*